(12) United States Patent
Saudan et al.

(10) Patent No.: US 10,538,468 B2
(45) Date of Patent: Jan. 21, 2020

(54) HYDROGENATION OF ALDEHYDE OR KETONE COMPOUNDS WITH FE/TRIDENTATE LIGANDS COMPLEXES

(71) Applicant: Firmenich SA, Geneva (CH)

(72) Inventors: Lionel Saudan, Geneva (CH); Jézabel Praz, Geneva (CH)

(73) Assignee: Firmenich SA, Geneva (CH)

( * ) Notice: Subject to any disclaimer, the term of this patent is extended or adjusted under 35 U.S.C. 154(b) by 45 days.

(21) Appl. No.: 15/580,456

(22) PCT Filed: Jun. 16, 2016

(86) PCT No.: PCT/EP2016/063893
§ 371 (c)(1),
(2) Date: Dec. 7, 2017

(87) PCT Pub. No.: WO2016/202925
PCT Pub. Date: Dec. 22, 2016

(65) Prior Publication Data
US 2018/0170843 A1   Jun. 21, 2018

(30) Foreign Application Priority Data
Jun. 17, 2015  (EP) .................... 15172581

(51) Int. Cl.
| | | |
|---|---|---|
| *C07C 29/145* | (2006.01) | |
| *B01J 31/18* | (2006.01) | |
| *C07C 29/141* | (2006.01) | |
| *B01J 31/20* | (2006.01) | |
| *B01J 31/22* | (2006.01) | |
| *B01J 31/24* | (2006.01) | |
| *C07F 15/02* | (2006.01) | |

(52) U.S. Cl.
CPC .......... *C07C 29/145* (2013.01); *B01J 31/189* (2013.01); *B01J 31/20* (2013.01); *B01J 31/2208* (2013.01); *B01J 31/2226* (2013.01); *B01J 31/24* (2013.01); *C07C 29/141* (2013.01); *C07F 15/02* (2013.01); *B01J 2231/643* (2013.01); *B01J 2531/842* (2013.01); *C07C 2601/10* (2017.05); *C07C 2601/14* (2017.05); *C07C 2601/16* (2017.05)

(58) Field of Classification Search
None
See application file for complete search history.

(56) References Cited

PUBLICATIONS

International Search Report and Written Opinion, application PCT/EP2016/063893 dated Sep. 26, 2016.
Bielinski et al., 'Lewis acid-assisted formic acid dehydrogenation using a pincer supported iron catalyst . . . ' J. Am. Chem. Soc. 2014, 136, 10234-10237.
Chakraborty et al., 'Iron-Based Catalysts for the Hydrogenation . . . ', JACS, 2014, 136, 7869-7872.
Danopoulos et al., 'The synthesis of tridentate dialkylamino . . . ', Polyhedron, 1990, vol. 9, No. 19, 2413-2418.
Koehne et al., 'Synthesis and Structure of Six-Coordinate . . . ', Inorg. Chem., 2014, 53, 2133-2143.
Lagaditis et al., 'Iron (I I) Complexes Containing . . . ', J. Am. Chem. Soc. 2014, 136, 1367-1380.
Lagaditis et al., 'Template Synthesis of Iron(II) Complexes Containing Tridentate . . . ', Inorg. Chem. 2010, 49, 1094-1102.
Langer et al., 'Efficient hydrogenation of ketones catalyzed . . . ', Angew. Chem. Int. Ed. 2011, 50, 2120-2124.
Langer et al., 'Iron Borohydride Pincer Complexes for the Efficient Hydrogenation . . . ', 2012, Chem. Eur. J., 18, 1196-7209.
Noyori et al., 'Asymmetric Catalysis by Architectural and Functional Molecular . . . ', Angew. Chem. Int. Ed. 2001, 40, 40-73.
Saudan, 'Hydrogenation of Esters', Sustainable Catalysis, Wiley & Sons, 2013, 37-61.

*Primary Examiner* — Clinton A Brooks
(74) *Attorney, Agent, or Firm* — Armstrong Teasdale LLP

(57) ABSTRACT

The present invention relates to the field of catalytic hydrogenation and, more particularly, to the use of Fe complexes with tridentate ligands, having one amino or imino coordinating group and two phosphino coordinating groups, in hydrogenation processes for the reduction of ketones or aldehydes, into the corresponding alcohol or diol, respectively.

9 Claims, No Drawings ations.

HYDROGENATION OF ALDEHYDE OR KETONE COMPOUNDS WITH FE/TRIDENTATE LIGANDS COMPLEXES

RELATED APPLICATIONS

This application is a 371 filing of International Patent Application PCT/EP2016/063893 filed 16 Jun. 2016, which claims the benefit of European patent application no 15172581.9 filed 17 Jun. 2015. The contents of which are incorporated herein by reference in their entirety.

TECHNICAL FIELD

The present invention relates to the field of catalytic hydrogenation and, more particularly, to the use of Fe complexes with tridentate ligands, in hydrogenation processes for the reduction of ketones or aldehydes into the corresponding alcohol or diol, respectively.

PRIOR ART

Reduction of ketone or aldehyde to the corresponding alcohol is one of the fundamental reactions in organic chemistry, and is used in a large number of chemical processes. In general, two main types of processes are known to achieve such a transformation. Such types of processes are the following:
a) hydride processes, in which a silyl or metal hydride salt, such as LiAlH$_4$, is used;
b) hydrogenation processes, in which molecular hydrogen is used.

From a practical point of view, hydrogenation processes are more attractive as they can be run using small amounts of catalyst (typically 10 to 1000 ppm relative to the substrate) and in the presence of small quantities or even in the absence of solvent. Furthermore, hydrogenation processes do not require the use of highly reactive and expensive hydrides, and do not produce important amounts of aqueous waste.

One of the mandatory and characterizing elements of hydrogenation processes is the catalyst or the catalytic system which is used to activate the molecular hydrogen in view of the reduction. The development of useful catalysts or catalytic systems for the hydrogenation of a carbonyl functional group represents still an important need in chemistry.

Amongst the few catalysts or catalytic systems known to perform such reductions one may cite the ruthenium/aminophosphine complexes, extensively reported in the literature (e.g. Noyori, R *Angew. Chem. Int. Ed.* 2001, 40, 40-73; Saudan, L. A. in Dunn, P. J.; Hii, K. K.; Krische, M. J.; Williams M. T. Editors. Sustainable Catalysis, J. Wiley & Sons, New Jersey; 2013, pp 37-61). However, such systems, although being highly performing, suffer from requiring highly expensive and toxic ruthenium metal.

Morris (see *Inorg. Chem.* 2010, 49, 1094) reported two Iron complexes with a PNP-pincer imine ligand having acetonitrile as ligand, and wherein no activity or use is reported or suggested. More recently, Morris (*J. Am. Chem. Soc.*, 2014, 136(22), 1367) disclosed the fine-tuning of the complex here-above by replacing the acetonitrile ligand by carbon monoxide and the use of this one as a catalyst for hydrogenation of ketone. However, this catalyst requires a preactivation with LiAlH$_4$ and are inefficient toward the reduction of α,β-unsaturated ketone.

Milstein (see *Angew. Chem. Int. Ed,* 2011, 50, 2120) reported an aldehyde, ketone hydrogenation using an iron complex with a tridentate pyridine derivative. The document shows weak selectivity on enones/enals as well as moderate activity toward if) standard aldehyde, ketone.

The hydrogenations described in these prior arts are always carried out in a presence of a base which represents a drawback for certain substrates leading, in such conditions, to formation of polymer instead of the alcohol product.

So there is a need for base-free hydrogenation process. One solution was proposed by Milstein (see *Chem. Eur. J.,* 2012, 18, 7196). Indeed, the use of [(i-Pr—PNP)Fe(CO)(HBH$_4$)] as catalyst, wherein the PNP ligand is a tridentate pyridine derivative, allows avoiding the addition of a base to activate the catalyst toward hydrogenation. Nevertheless, these base-free conditions have not improved the selectivity issue on enones/enals and the activity toward standard ketone. Furthermore the addition of base is needed in order to hydrogenate aldehydes.

Therefore, there is a need for hydrogenation processes using catalysts or pre-catalysts with an alternative activation mode free of base and presenting a broader spectrum of substrates and if possible with enhanced selectivity.

DESCRIPTION OF THE INVENTION

In order to overcome the problems aforementioned, the present invention relates to processes for the reduction by hydrogenation, using molecular H$_2$, of a C$_3$-C$_{70}$ substrate containing one or two ketones or aldehydes into the corresponding alcohol, or diol, characterized in that said process is carried out in the presence of at least one catalyst in the form of a iron complex of a tridentate ligand wherein the coordinating groups consist of one amino or imino group and two phosphino group and optionally a salt of formula MX wherein M is an alkali metal cation and X a non-coordinating mono anion.

By the expression "in the presence of at least one catalyst . . . and optionally a salt of formula MX . . . " or the similar, it is meant that the reaction can be carried out in present of catalyst or in presence of catalyst and MX.

According to an embodiment of the invention, said amino group is a secondary (i.e. NH) amino group.

According to a particular embodiment of the invention, the substrate can be a compound of formula (I)

wherein R$^a$ and R$^b$, taken together, represent a C$_3$-C$_{20}$, preferably C$_4$-C$_{20}$, hydrocarbon group, optionally substituted and optionally comprising one, two or three oxygen or nitrogen atoms; or, when said R$^a$ and R$^b$ are taken separately, R$^a$ represents a hydrogen atom or a R$^b$ group; and R$^b$ represents a C$_1$-C$_{30}$ hydrocarbon group, optionally substituted and optionally comprising one, two or three oxygen or nitrogen atoms.

The corresponding alcohol (i.e (II-a)), is of formula

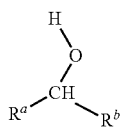
(II-a)

wherein $R^a$ and $R^b$ are defined as in formula (I).

It is understood that by " . . . hydrocarbon group . . . " it is meant that said group can be in the form of a linear, branched or cyclic aromatic, alkyl, alkenyl, alkandienyl or alkynyl group, e.g., a cyclic alkyl group, or can also be in the form of a mixture of said type of groups, e.g. a specific group may comprise a linear alkyl, a branched alkandienyl (e.g. having one or more carbon-carbon double bonds), a (poly) cyclic alkyl and an aryl moiety, unless a specific limitation to only one type is mentioned. Similarly, in all the below embodiments of the invention, when a group is mentioned as being in the form of more than one type of topology (e.g. linear, cyclic or branched) and/or unsaturation (e.g. alkyl, aromatic or alkenyl), it is meant also a group which may comprise moieties having any one of said topologies or unsaturations, as explained above. Similarly, in all the below embodiments of the invention, when a group is mentioned as being in the form of one type of unsaturation, (e.g. alkyl), it is meant that said group can be in any type of topology (e.g. linear, cyclic or branched) or having several moieties with various topologies.

According to any one of the embodiments of the invention, said aldehyde or ketone is one that will provide an alcohol, or a diol, that is useful in the pharmaceutical, agrochemical or perfumery industry as final product or as an intermediate. Particularly preferred substrate is an aldehyde or ketone, which will provide an alcohol, or diol, which is useful in the perfumery industry as final product or as an intermediate.

According to any one of the embodiments of the invention, the substrate is a $C_5$-$C_{30}$ compound of formula (I), or even a $C_5$-$C_{20}$ compound of formula (I).

According to any one of the embodiments of the invention, one may cite as substrate the one wherein $R^a$ represents a hydrogen atom or a $R^b$ group, and each $R^b$, when taken separately, represents simultaneously or independently a linear, branched or cyclic $C_1$-$C_{30}$ aromatic, alkyl, alkenyl or alkanedienyl group optionally substituted and optionally comprising one or two oxygen or nitrogen atoms; or $R^a$ and $R^b$ are bonded together and form a $C_4$-$C_{20}$ saturated or unsaturated linear, branched, mono-, di- or tri-cyclic group, optionally substituted and optionally comprising one or two oxygen or nitrogen atoms.

According to any one of the embodiments of the invention, one may cite as substrate those wherein $R^a$ represents a hydrogen atom or a $R^b$ group, and each $R^b$, when taken separately, represent simultaneously or independently a linear, branched or cyclic $C_3$-$C_{18}$ aromatic, alkyl, alkenyl or alkanedienyl group optionally substituted; or $R^a$ and $R^b$ are bonded together and form a $C_5$-$C_{20}$ saturated or unsaturated linear, branched, mono-, di- or tri-cyclic group, optionally substituted.

According to any one of the above embodiments of the invention, when $R^b$ is an alkenyl or alkadienyl group, then said group is an alk-1-enyl or an alka-1,3-dienyl group (i.e. the carbon carbon double bonds are conjugated with the carbonyl group).

According to a prefer embodiment $R^b$ is a $C_{3-18}$ alk-1-enyl group wherein the carbon carbon double bond is di or tri substituted; i.e. compound of formula (I) is a α,β-unsaturated ketone or aldehyde also knowns as an enol or an enal. Even more preferably, $R^b$ is an alk-1-enyl group wherein the carbon carbon double bond is di-substituted.

According to any one of the above embodiments of the invention, when $R^a$ is a hydrogen atom, $R^b$ may represent in particular a branched or cyclic hydrocarbon group wherein the branching is in the alpha position relative to the CHO group of the substrate.

Possible substituents of $R^a$ and $R^b$ are one, two or three halogen, $OR^c$, $NR^c_2$ or $R^c$ groups, in which $R^c$ is a hydrogen atom, a halogenated $C_1$-$C_2$ group or a $C_1$ to $C_{10}$ cyclic, linear or branched alkyl, or alkenyl group, preferably a $C_1$ to $C_4$ linear or branched alkyl or alkenyl group. As other possible substituents one may also cite a group $COOR^c$, which can also be reduced to the corresponding alcohol during the invention's process, according to the molar amount of $H_2$ used, as well known by a person skilled in the art.

According to a particular aspect of the invention, the possible substituents of $R^a$ and $R^b$ are one or two halogen, $OR^c$, $NR^c_2$ or $R^c$ groups, in which $R^c$ is a hydrogen atom, a $C_1$ to $C_6$ cyclic, linear or branched alkyl, or alkenyl group, preferably a $C_1$ to $C_4$ linear or branched alkyl or alkenyl group.

Non-limiting examples of substrates of formula (I) are the following:

$C_{3-14}$ aldehydes such as:
a $C_{3-10}$ alkanal, a $C_{3-10}$ 2-alkenal, a $C_{3-10}$ 2-methyl-2-alkenal, a $C_{5-10}$ 2,4-dienal, a 3-alkyl-3-benzene-prop-2-enal, a 3-alkyl-2-methyl-3-benzene-prop-2-enal, a $C_{7-10}$-benzenecarbaldehyde, a $C_{5-10}$ cycloalk-1-ene-1-carbaldehyde, a $C_{4-12}$ 2-methylen-aldehyde; wherein the underlined compounds are known to be particularly base-sensitive substrates;

$C_{3-17}$ ketones such as:
a di($C_{1-12}$ alkyl) ketone, a $C_4$-$C_{12}$ cyclic-ketone, a cyclopentenone alpha substituted by a $C_{5-12}$ hydrocarbon group, a cylohex-2-en-1-one substituted by zero to three methyl groups, a cyclohexenone alpha substituted by a $C_{6-12}$ hydrocarbon group, a substituted aryl $C_{1-12}$-alkyl ketone, a substituted aryl $C_{2-12}$-1-alkene methyl ketone, a substituted cyclohexenyl $C_{2-6}$-1-alkene methyl ketone, a $C_{2-12}$-1-alkene methyl ketone, a $C_{2-15}$-2-alkene-1,1-dimethyl methyl ketone, a $C_{2-15}$-2-alkyl-1,1-dimethyl methyl ketone; wherein the underlined compounds are known to be particularly base-sensitive substrates.

The process of the invention is characterized by the use, as catalyst or pre-catalyst (hereinafter referred to as complexes unless specified otherwise), of an iron complex as described above. The complex can be in the form of an ionic or neutral species.

According to an embodiment of the invention, the iron complex can be of the general formula

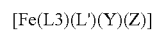
[Fe(L3)(L')(Y)(Z)]     (1)

wherein L3 represents a tridentate ligand wherein the coordinating groups consist of one amino or imino group and two phosphino groups;
L' represents a CO or $C_{1-11}$ isonitrile compound;
Y represents a hydrogen atom or a $C_1$-$C_{14}$ carboxylic radical; and
Z represents a hydroxyl group, a $C_1$-$C_{14}$ carboxylic radical or a linear $C_1$-$C_{14}$ alkoxy radical.

By "$C_1$ to 14 carboxylic radical" or the similar, it is meant the normal meaning in the art, i.e. a RCOO radical wherein R group is a hydrogen atom or a $C_1$ to $C_{13}$ hydrocarbon group optionally comprising one or two oxygen or nitrogen atoms. Preferably R is an alkyl or aromatic group optionally substituted and optionally comprising one or two oxygen or nitrogen atoms.

The person skill in the art is well aware than Y and/or Z could be in the coordinative sphere of the Iron or could be decoordinated, in particular when Y and/or Z represent an alkoxy or carboxylic radical.

In a particular embodiment of the invention, said L3 ligand may be a $C_6$-$C_{40}$, or even a $C_6$-$C_{30}$, compound.

According to any embodiment of the invention, in formula (1), Y may represent a hydrogen atom, or a $C_1$ to $C_8$ carboxylic radical such as a HCOO, $CH_3COO$ or $CH_3CH_2COO$ radical. More preferably, Y may represent a hydrogen atom, According to any embodiment of the invention, in formula (1), Z may represent, hydroxy radical.

According to any embodiment of the invention, in formula (1), Z may represent a $C_1$-$C_{14}$ carboxylic radical optionally substituted by one to three ether functional groups. Preferably, Z may represent a $C_1$ to $C_8$ alkyl carboxylic radical such as a HCOO, $CH_3COO$ or $CH_3CH_2COO$ radical optionally substituted by one to three ether functional groups or a $C_7$ to $C_{13}$ aromatic carboxylic radical optionally substituted by one to three alkyl or ether groups such as 4-phenylbenzoicCOO, 3,5-dimethylphenylCOO or p-MeOphenylCOO. More preferably, Z may represent a $C_1$ to $C_6$ alkyl carboxylic radical or a $C_8$ to $C_{13}$ aromatic carboxylic radical optionally substituted by an alkyl or ether groups. More preferably, Z may represent a $C_1$ to $C_5$ alkyl carboxylic radical or a $C_8$ to $C_9$ aromatic carboxylic radical wherein the aromatic ring is preferably substituted by an electron donating group such as a methyl or a methoxy group. More preferably, Z may represent, a $C_1$ to $C_4$ alkyl carboxylic radical. Even more preferably, Z may represent a formate, an acetate or a pivalate radical. Even more preferably, Z may represent a formate or an acetate radical. Said complex, wherein Z represents a formate has been only reported in Lewis acid-assisted formic acid dehydrogenation reaction (J. Am. Chem. Soc. 2014, 136, 10234-10237).

According to another embodiment, Z may represent an acetate or a pivalate radical.

According to any embodiment of the invention, in formula (1), Z may represent a linear $C_1$-$C_{14}$ alkoxy. Preferably, Z may represent, a linear $C_1$ to $C_6$ alkoxy radical, such as a methoxy, ethoxy, propoxy or butoxy radical. More preferably, Z may represent a linear $C_1$ to $C_4$ alkoxy radical. More preferably, Z may represent a methoxy or ethoxy radical, preferably a methoxy radical.

By the term "an electron donating group" or the similar, it is meant the normal meaning in the art, i.e. an atom or functional group capable of donating some of its electronic density to the adjacent aromatic system, e.g. alkoxy, alkyl or amine group.

According to any embodiment of the invention, L' may represent a CO.

According to any one of the above-mentioned embodiments, the tridentate ligand L3 can be a compound of one of the formula wherein the dotted line indicates a single or double bond;
z is 0 or 1 when the carbon-nitrogen bond with the dotted line represents a double or single bond respectively;
$R^1$ and $R^2$, when taken separately, represent, simultaneously or independently, a linear, branched or cyclic $C_1$ to $C_{10}$ alkyl or alkenyl group optionally substituted, a $C_6$ to $C_{10}$ aromatic group optionally substituted; said groups $R^1$ and $R^2$, when taken together, may form a saturated or unsaturated ring optionally substituted, having 5 to 10 atoms and including the phosphorus atom to which said $R^1$ and $R^2$ groups are bonded;
$R^6$ and $R^7$ represent, simultaneously or independently, a hydrogen atom, a linear, branched or cyclic $C_1$ to $C_6$ alkyl or alkenyl group optionally substituted, a $C_6$-$C_{10}$ aromatic group optionally substituted; when the dotted line represent a single bond, two $R^6$ taken together, may form a saturated heterocycle, optionally substituted and optionally containing one or two additional nitrogen or oxygen atoms, containing 5 to 10 atoms and including the N atom and the carbon atoms to which said $R^6$ groups are bonded respectively; and
Q represents:
a group of formula

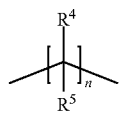

(i)

wherein n is an integer from 1 to 3, and
$R^4$ and $R^5$ represent, simultaneously or independently, a hydrogen atom, a linear, branched or cyclic $C_1$ to $C_6$ alkyl or alkenyl group optionally substituted, a $C_6$-$C_{10}$ aromatic group optionally substituted; two distinct $R^4$ and/or $R^5$ groups, taken together, may form a $C_5$ to $C_8$, saturated ring optionally substituted, including the carbon atoms to which each of said $R^4$ or $R^5$ group is bonded; or
a diphenyl, dinaphthyl, $C_5$-$C_{12}$ metallocediyl, phenylene or naphthylene group optionally substituted.

According to any embodiment of the invention, by "aromatic group or ring" it is meant a phenyl or naphthyl derivative.

For the sake of clarity, by the expression "wherein one dotted line represents a single or double bond", or the similar, it is meant the normal meaning understood by a person skilled in the art, i.e. that the whole bonding (solid and dotted line) between the carbon and nitrogen atoms connected by said dotted line, is a carbon-nitrogen single or double bond.

According to any one of the above-mentioned embodiments, the tridentate ligand L3 can be a compound of one of the formula

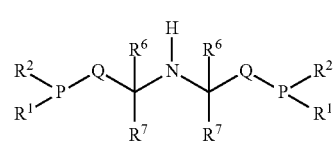

(B)

wherein the $R^1$, $R^2$, $R^6$ and $R^7$ have the meaning indicates in formula (A).

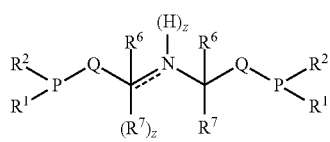

(A)

According to any embodiment of the invention, $R^1$ and $R^2$, when taken separately, represent, simultaneously or independently, a linear, branched or cyclic $C_1$ to $C_{10}$ alkyl group optionally substituted, a $C_6$-$C_{10}$ phenyl or naphthyl group optionally substituted; said groups $R^1$ and $R^2$, when taken together, may form a saturated ring optionally substituted, having 5 to 10 atoms and including the phosphorus atom to which said $R^1$ and $R^2$ groups are bonded.

According to any embodiment of the invention, $R^1$ and $R^2$ are taken separately and each represent, simultaneously or independently, a linear, branched or cyclic $C_1$, or even $C_3$, to $C_6$ alkyl group optionally substituted, a phenyl group optionally substituted.

According to any embodiment of the invention, $R^6$ and $R^7$ represent, simultaneously or independently, a hydrogen atom, a linear, branched or cyclic $C_1$ to $C_6$ alkyl group optionally substituted, a phenyl group optionally substituted; when the dotted line represent a single bond, two $R^6$ taken together, may form a saturated heterocycle, optionally substituted and optionally containing one additional nitrogen or oxygen atoms, containing 5 or 6 atoms and including the N atom and the carbon atoms to which said $R^6$ groups are bonded respectively.

According to any embodiment of the invention, one or two $R^7$ are hydrogen atoms. Similarly one or two $R^6$ are hydrogen atoms.

According to any embodiment of the invention, Q represents:

a group of formula

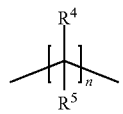

wherein n is 1 or 2, and $R^4$ and $R^5$ represent, simultaneously or independently, a hydrogen atom, a linear, branched or cyclic $C_1$ to $C_6$ alkyl group optionally substituted, a $C_6$-$C_{10}$ phenyl or naphthyl group optionally substituted; or a $C_5$-$C_{12}$ ferrocenediyl, 1,2-phenylene or 1,2- or 2,3-naphthylene group optionally substituted.

According to any embodiment of the invention, Q represents a group of formula (i)
wherein n is 1 or 2, and $R^4$ and $R^5$ represent, simultaneously or independently, a hydrogen atom, a linear, branched or cyclic $C_1$ to $C_6$ alkyl group optionally substituted, a phenyl group optionally substituted.

According to any embodiment of the invention, Q represents a linear methylene or ethylene group optionally substituted.

According to any embodiment of the invention, possible substituents of $R^4$, $R^5$, $R^6$ and $R^7$ are one or two halogen, $C_1$ to $C_{10}$ alkoxy groups, halo- or perhalo-hydrocarbon, COOR, $NR_2$, quaternary amine or R groups, wherein R is a $C_1$ to $C_6$ alkyl, or a $C_5$ to $C_{12}$ cycloalkyl, aralkyl (such as benzyl, phenethyl etc.) or aromatic group, the latter being also optionally substituted by one, two or three halogen, sulfonates groups or $C_1$-$C_8$ alkyl, alkoxy, amino, nitro, sulfonates, halo- or perhalo-hydrocarbon or ester groups. By "halo- or perhalo-hydrocarbon" it is meant groups such as $CF_3$ or $CClH_2$ for instance.

According to any embodiment of the invention, possible substituents of $R^4$, $R^5$, $R^6$ and $R^7$ are one or two halogen, $C_1$ to $C_6$ alkoxy groups, COOR, $NR_2$, quaternary amine or R groups, wherein R is a $C_1$ to $C_6$ alkyl, or a $C_5$ to $C_{12}$ cycloalkyl, aralkyl (such as benzyl, phenethyl etc.) or aromatic group, the latter being also optionally substituted by one, two or three halogen, sulfonates groups or $C_1$-$C_8$ alkyl, alkoxy, amino, nitro, sulfonates, halo- or perhalo-hydrocarbon or ester groups.

Possible substituents of $R^1$ and $R^3$ and Q, in particular when said groups are or contain phenyl or aromatic groups or moieties, one to three $C_1$ to $C_5$ alkoxy groups, $C_1$ to $C_4$ alkyl groups, or NR groups, wherein R is a $C_1$ to $C_6$ alkyl $C_5$ to $C_6$ cycloalkyl.

The processes of the invention are particularly attractive when L3 represents a ligand of the formula (C):

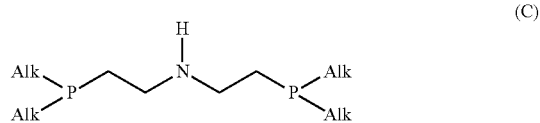

wherein Alk is a $C_{3-10}$, or even $C_{3-6}$, branched or cyclic alkyl group. Preferably Alk may represent an isopropyl group.

According to any embodiment of the invention, the process of the invention is performed in absence of base.

Certain complexes according to the invention are also new. Therefore, another object of the present invention is a complex of formula

[Fe(L3)(L')(Y)(Z)]  (1)

wherein L3, L' and Y have the same meaning as above; and Z represents a $C_2$ to $C_6$ alkyl carboxylic radical or a $C_7$ to $C_{14}$ aromatic carboxylic radical; i.e. Z does not represent a formate.

The ligands described above can be obtained by applying standard general methods which are well known in the state of the art and by the person skilled in the art. Therefore, their preparation does not require a specific description. For example one may revert to Edwards, P. G. *Polyhedron* 1990, 9, 2413-2418.

In a general way, the complexes of formula (1) or (2) can be prepared and isolated prior to their use in the process according to the general methods described in the literature. A method is described in the Example.

Moreover, the complexes can be prepared in situ, by several methods, without isolation or purification, just before their use as described in the Example or also one may use as starting complexes the ones of formula

[Fe(L3')(L')Y]  (3)

wherein L3' represents a L3 with deprotonated amine; i.e. L3' is an amido ligand, and L' and Y are as defined above;

which are then reacted with a $C_1$-$C_{14}$ carboxylic acid.

A salt of formula MX wherein M is an alkali metal cation and X a non-coordinating mono anion can be optionally added in order to carry out the process of the present invention.

According to any one of the above embodiments, M represents an alkali metal cation such as Na, K, Cs or Li and X represents a non-coordinative anion such as $BF_4^-$, $CF_3SO_3^-$, $PO_4^{3-}$, $F^-$, $PF_6^-$, $BAr^F_4^-$, $Cl^-$ or $CF_3COO^-$.

According to a particular embodiment, MX may be selected from the group consisted of $NaBF_4$, $KBF_4$, $CsBF_4$, LiF and $K_3PO_4$. Preferably MX is $NaBF_4$, $KBF_4$ or $CsBF_4$, even more preferably MX is $KBF_4$.

According to a prefer embodiment, the process of the invention is carried out in presence of a salt of formula MX.

As previously mentioned the processes of the invention consist in the hydrogenation of a substrate using an iron complex and optionally MX. A typical process implies the mixture of the substrate with the iron complex and optionally MX and a solvent, and then treating such a mixture with molecular hydrogen at a chosen pressure and temperature.

The complexes of the invention, an essential parameter of the process, can be added to the reaction medium in a large range of concentrations. As non-limiting examples, one can cite as complex concentration values those ranging from 50 ppm to 50000 ppm, relative to the amount of substrate. Preferably, the complex concentration will be comprised between 100 and 20000 ppm, or even between 1000 and 10000 ppm. It goes without saying that the optimum concentration of complex will depend, as the person skilled in the art knows, on the nature of the latter, on the nature of the substrate and on the pressure of $H_2$ used during the process, as well as the desired time of reaction.

Useful quantities of MX, added to the reaction mixture, may be comprised in a relatively large range. One can cite, as non-limiting examples, ranges between 0.0005 to 0.2 molar equivalents, relative to the substrate, preferably 0.001 to 0.10, and even more preferably between 0.05 to 0.10 molar equivalents.

The hydrogenation reaction can be carried out in the presence or absence of a solvent. When a solvent is required or used for practical reasons, then any solvent current in hydrogenation reactions can be used for the purposes of the invention. Non-limiting examples include aromatic solvents such as toluene or xylene, hydrocarbon solvents such as hexane, heptane or cyclohexane, ethers such as tetrahydrofuran or MTBE, polar solvents such as primary or secondary alcohols such as isopropanol or ethanol, or mixtures thereof. Preferably, the solvent is selected from the group consisting of THF, toluene and heptane. The choice of the solvent is a function of the nature of the complex and the person skilled in the art is well able to select the solvent most convenient in each case to optimize the hydrogenation reaction.

In the hydrogenation process of the invention, the reaction can be carried out at a $H_2$ pressure comprised between $10^5$ Pa and $80 \times 10^5$ Pa (1 to 80 bar) or even more if desired. Again, a person skilled in the art is well able to adjust the pressure as a function of the catalyst load and of the dilution of the substrate in the solvent. As examples, one can cite typical pressures of 1 to $50 \times 10^5$ Pa (1 to 50 bar).

According to a particular embodiment of the invention, the atmosphere of the reaction medium may also contain about 0.001 and 0.10%, or even 0.01 and 0.05%, of CO relative to the molar amount of $H_2$.

The temperature at which the hydrogenation can be carried out is comprised between 0° C. and 120° C., more preferably in the range of between 20° C. and 100° C., or even between 50° C. and 100° C. Of course, a person skilled in the art is also able to select the preferred temperature as a function of the presence of MX, of the melting and boiling point of the starting and final products as well as the desired time of reaction or conversion.

The invention will now be described in further detail by way of the following examples, wherein the temperatures are indicated in degrees centigrade and the abbreviations have the usual meaning in the art.

All the procedures described hereafter have been carried out under an inert atmosphere unless stated otherwise. Hydrogenations were carried out either in open glass tubes placed inside a stainless steel autoclave or directly in the autoclave. $H_2$ gas (99.99990%) was used as received. All substrates and solvents were distilled from appropriate drying agents under Ar. NMR spectra were recorded on a Bruker AM-400 ($^1$H at 400.1 MHz, $^{13}$C at 100.6 MHz, and $^{31}$P at 161.9 MHz) spectrometer and normally measured at 300 K, in $CD_2Cl_2$ unless indicated otherwise. Chemical shifts are listed in ppm downfield from tetramethylsilane. $^{31}$P NMR chemical shifts are reported in ppm downfield from $H_3PO_4$ and referenced to an external 85% solution of phosphoric acid in $D_2O$ as standard.

EXAMPLES

Example 1

Preparation of carbonyl dibromo bis[2-(di-isopropylphosphino)ethyl] amine iron (II) (Fe(L-1)(CO)(Cl$_2$)

(prepared according to: I. Koehne, T. J. Schmeier, E. A. Bielinski, C. J. Pan, P. O. Lagaditis, W. H. Bernskoetter, M. K. Takase, C. Würtele, N. Hazari, S. Schneider, *Inorg. Chem.* 2014, 53, 2133-2143):

Under an argon atmosphere, to a stirred suspension of iron(II) chloride (620 mg, 4.89 mmol) in THF (21 mL) in a heavy wall glass tube was added bis(2-(diisopropylphosphino)ethyl)amine, L-1, (prepared according to A. A. Danopoulos, A. R. Wills, P. G. Edwards, *Polyhedron* 1990 9, 2413-2418) (1.5 g, 4.91 mmol) at 25° C. More THF (3×1 mL) was added to rinse. The milky white solution was heated at 65° C. during 1 h. After cooling to room temperature, the suspension was placed under CO atmosphere (2 bar), after purging with CO (3×1 bar). The mixture was stirred under CO atmosphere overnight. After 10 min, a deep purple solution was obtained with total dissolution of the solid. Evaporation of the solvent under vacuum afforded a deep purple solid which was dissolved in DCM (10 mL) and added drop wise to pentane (50 mL). The suspension was concentrated following by addition of more pentane (10 mL), and concentrated until the supernatant became clear. The purple solid was filtrated, washed with pentane (2×5 mL) and finally dried under vacuum (0.1 mbar/1 h). The desired complex was obtained as a deep purple solid (2.133 gr, 95% yield).

Example 2

Preparation of carbonyl hydridobromo bis[2-(di-isopropylphosphino)ethyl] amine iron (II) (Fe(L-1)(CO)(H)(Cl))

(prepared according to: a) I. Koehne, T. J. Schmeier, E. A. Bielinski, C. J. Pan, P. O. Lagaditis, W. H. Bernskoetter, M. K. Takase, C. Würtele, N. Hazari, S. Schneider, *Inorg. Chem.* 2014, 53, 2133-2143; b) S. Chakraborty, H. Dai, P. Bhattacharya, N. T. Fairweather, M. S. Gibson, J. A. Krause, H. Guan, *J. Am. Chem. Soc.* 2014, 136, 7869-7872):

Under an argon atmosphere, a 50 mL oven-dried Schlenk flask equipped with a stirring bar was charged with (Fe(L-1)(CO)Cl$_2$) (500 mg, 1.087 mmol) and NaBH$_4$ (44.5 mg, 1.176 mmol). Adding EtOH (40 mL) to this mixture at 0° C., resulted in a yellow solution in few minutes. The resulting mixture was gradually warmed to room temperature and then stirred for additional 16 h. Removal of the volatiles under vacuum afforded an orange brown solid, which was treated with toluene (30 mL) and then filtered through a pad of Celite to give an orange solution. Evaporating the solvent under vacuum yielded the desired compound as a bright orange powder (419 mg, 91% yield).

Example 3

Preparation of carbonyl Amido bis[2-(di-isopropylphosphino)ethyl] amine iron (II) (Fe(L-1)(CO)(H))

(prepared according to: E. A. Bielinski, P. O. Lagaditis, Y. Zhang, B. Q. Mercado, C. Würtele, W. H. Bernskoetter, N. Hazari, S. Schneider, *J. Am. Chem. Soc.* 2014, 136, 10234-10237):

Under an argon atmosphere, a schlenk was charged with (Fe(L-1)(CO)(H)Cl (340 mg, 0.8 mmol) and KO$^t$Bu (98 mg, 0.87 mmol). Upon addition of THF (20 mL) at room temperature an immediate colour change from yellow to red-purple was observed. The suspension was stirred for 30 minutes at room temperature and the solvent was evaporated in vacuum. The red-purple residue was extracted with pentane, filtered over Celite and then the solvent was removed. The desired red-purple complex was dried under vacuum (0.1 mbar, 1 h) to give a dark-purple solid (305 mg, 98% yield).

Example 4

Preparation of carbonyl hydridoformate bis[2-(di-isopropylphosphino)ethyl] amine iron (II) (Fe(L-1)(CO)(H)(OC(O)H)) (C1)

(prepared according to: E. A. Bielinski, P. O. Lagaditis, Y. Zhang, B. Q. Mercado, C. Würtele, W. H. Bernskoetter, N. Hazari, S. Schneider, *J. Am. Chem. Soc.* 2014, 136, 10234-10237.):

Under an argon atmosphere, a solution of formic acid (30 mg, 0.65 mmol) in THF (2 mL) was added to Fe(L-1)(CO)H (250 mg, 0,642 mmol) in THF (3 mL) at room temperature. The magenta mixture changed directly to a green-yellow solution. The mixture was stirred for 10 min at room temperature after which the solvent was evaporated and the residue was dissolved in pentane filtered and the solvent evaporated to give a yellow brown oily solid. The crude was triturated with pentane cooled to −20° C. then after removing of the solvent a yellow solid was obtained (220 mg, 79% yield).

Example 5

Preparation of carbonyl hydridopivalate bis[2-(di-isopropylphosphino)ethyl] amine iron (II) (Fe(L-1)(CO)(H)(OC(O)$^t$Bu)) (C2)

Under an argon atmosphere, a solution of pivalic acid (2.1 ml at 0.11M, 0.23 mmol) in THF was added to Fe(L-1)(CO)H (93 mg, 0.239 mmol) in THF (3 mL) at room temperature. The magenta mixture changed directly to a green-yellow solution. The solution was stirred for 10 min at room temperature after which the solvent was evaporated and the residue was dissolved in pentane filtered and the solvent evaporated to give an orange-yellow solid (117 mg, >99% yield).

$^1$H-NMR (C$_6$D$_6$, 500 MHz) δ: 9.56 (bs, 1H), 2.85-2.7 (m, 2H), 2.74-2.86 (m, 2H), 1.97-2.05 (m, 2H), 1.71-1.83 (m, 4H), 1.63 (dd, 7.5, 15 Hz, 8H), 1.35 (s, 9H), 1.21 (dd, 7.2, 14.8 Hz, 6H), 1.12 (dd, 5.9, 11 Hz, 6H), 0.88 (dd, 6.8, 13 Hz, 6H), −25.7 (t, 50.6 Hz, 1H).

$^{13}$C-NMR (C$_6$D$_6$, 100 MHz) δ: 189.91 (s, C, OC(O)), 53.7 (t, CH$_2$, JCP=6.2 Hz, NHCH$_2$), 40.8 (s, C, C(CH$_3$)$_3$), 29.8 (t, CH$_2$, JCP=7.1 Hz, NHCH$_2$P), 28.9 (s, CH$_3$, C(CH$_3$)$_3$), 28.0 (t, CH, JCP=7.9 Hz, PCH(CH$_3$)$_2$), 25.3 (t, 2C, JCP=12.6 Hz, PCH(CH$_3$)$_2$), 21.4 (t, CH$_3$, JCP=2.3 Hz), 20.4 (t, CH$_3$, JCP=2.3 Hz), 19.2 (s, CH$_3$), 17.8 (t, CH$_3$, JCP=2.3 Hz) CO resonance not detected.

$^{31}$P{$^1$H}-NMR (C$_6$D$_6$, 200 MHz): 96.7 (d, JPH=23.59 Hz).

Example 6

Preparation of carbonyl hydridoacetate bis[2-(di-isopropylphosphino)ethyl] amine iron (II) (Fe(L-1)(CO)(H)(OC(O)Me)) (C3)

Under an argon atmosphere, a solution of acetic acid (2.1 ml at 0.11M, 0.23 mmol) in THF was added to Fe(L-1)(CO)H (90.6 mg, 0.23 mmol) in THF (3 mL) at room temperature. The magenta mixture changed directly to a green-yellow solution. The solution was stirred for 10 min at room temperature after which the solvent was evaporated and the residue was dissolved in pentane filtered and the solvent evaporated to give an orange-yellow solid (102 mg, 98% yield).

$^1$H-NMR (C$_6$D$_6$, 500 MHz) δ: 9.44 (bs, 1H), 2.88-2.71 (m, 2H), 2.19-2.16 (m, 2H), 2.09 (s, 3H), 1.97-1.93 (m, 2H), 1.87-1.81 (m, 2H), 1.78-1.70 (m, 2H), 1.66-1.62 (m, 2H), 1.55 (q, J=7.3 Hz, 6H), 1.22-1.16 (m, 12H), 0.91 (dd, 6.8, 13.6 Hz, 6H), −25.7 (t, 50.2 Hz, 1H).

$^{13}$C-NMR (C$_6$D$_6$, 100 MHz) δ: 183.0 (s, C, OC(O)), 53.6 (t, CH$_2$, JCP=6.13 Hz, NHCH$_2$), 29.3 (t, CH$_2$, JCP=6.92 Hz, NHCH$_2$P), 28.2 (t, CH, JCP=8 Hz, PCH(CH$_3$)$_2$), 26.5 (s, CH$_3$), 26.0 (t, 2C, JCP=12.7 Hz, PCH(CH$_3$)$_2$), 20.4 (s, CH$_3$), 20.0 (s, CH$_3$), 19.1 (s, CH$_3$), 18.2 (s, CH$_3$), CO resonance not detected.

$^{31}$P{$^1$H}-NMR (C$_6$D$_6$, 200 MHz): 95.78 (d, JPH=19.9 Hz, 98%), 52.2 (s, Free oxidized ligand, 0.8%), −2.04 (s, free ligand)

Example 7

Catalytic Hydrogenation of Acetophenone Using Complexes Fe(L-1)(CO)(H)(OC(O)R)

A typical experimental procedure is as follows:

In a glow box under argon, test tubes were charged successively with the desired complexes Fe(L-1)(CO)(H)(OC(O)R) (0.25-0.5 mol %) and with KBF$_4$ (5-10 mol %) or without any additive. Then a solution of acetophenone (3 mmol) dissolved in THF (2 mL) was added. The tubes were then placed in a parallel hydrogenation apparatus and heated to the corresponding temperature, then pressurised with hydrogen gas at 20 bar and mechanically stirred. After 8 h, the parallel hydrogenation apparatus was cooled to room temperature, depressurized, and each tube analysed by GC (DB-Wax).

Under these conditions several complexes Fe(L-1)(CO)(H)(OC(O)R) as reported in Table 1 were tested. The results are reported in Table 2.

TABLE 1

Structures and names of complexes Fe(L-1)(CO)(H)(OC(O)R) used

| Complexes | Structure | Name |
|---|---|---|
| C1 | [structure] | Carbonyl hydrido formate bis[2-(di-isopropylphosphino)ethyl] amine iron (II) Fe(L-1)(CO)(H)(OC(O)H) |
| C2 | [structure] | Carbonyl hydrido pivalate bis[2-(di-isopropylphosphino)ethyl] amine iron (II) Fe(L-1)(CO)(H)(OC(O)$^t$Bu) |
| C3 | [structure] | Carbonyl hydrido acetate bis[2-(di-isopropylphosphino)ethyl] amine iron (II) Fe(L-1)(CO)(H)(OC(O)Me) |
| C4 | [structure] | Carbonyl hydrido formate bis[2-(di-ethylphosphino)ethyl] amine iron (II) Fe(L-2)(CO)(H)(OC(O)H) |

TABLE 2

Hydrogenation of acetophenone using isolated complexes Fe(L-1)(CO)(H)(OC(O)R)

| Test | Complexes | C/MX2 | T (° C.) | Conv. | ROH |
|---|---|---|---|---|---|
| 1 | C1 | 5000/0 | 50 | 73 | 73 |
| 2 | C1 | 5000/0 | 100 | >99 | 99.9 |
| 3 | C1 | 5000/100000 | 50 | >99 | >99 |
| 4 | C1 | 2500/100000 | 50 | >99 | >99 |
| 5 | C1 | 2500/5000 | 50 | 90 | 90 |
| 6 | C1 | 2500/0 | 50 | 67 | 67 |
| 7 | C2 | 5000/0 | 100 | 89 | 89 |
| 8 | C2 | 2500/100000 | 100 | 85 | 85 |
| 9 | C2 | 2500/50000 | 100 | 85 | 85 |
| 10 | C2 | 2500/0 | 100 | 60 | 60 |
| 11 | C3 | 5000/100000 | 100 | >99 | 99 |
| 12 | C4 | 2500/100000 | 50 | 56 | 56 |
| 13 | C4 | 2500/0 | 50 | 23 | 23 |

C/MX2: Catalyst/KBF$_4$ ratio in ppm relative to the substrate.
Conv.: Conversion (in %, analysed by GC) of acetophenone to 1-phenyl ethanol after 8 hours.
Reaction conditions: H$_2$ gas (20 bar), 50° C. or 100° C., THF (1.5M).
ROH: amount of 1-phenyl ethanol in percent in the reaction mixture as analysed by GC

Example 8

Catalytic Hydrogenation of Acetophenone Using Complexes Fe(L-1)(CO)(H)(OC(O)R) Generated In-Situ A typical experimental procedure is as follows:
Solutions Stock:
A solution of carboxylic acid 0.11M in THF.
A solution of complex Fe(L-1)(CO)H 0.018M in THF.
A solution of 3M of acetophenone in THF.

In 1 ml solution of Fe(L-1-H)(CO)(H) (0.018 M) was added 0.2 mL of the carboxylic acid solution (0.11 M). A solution of Fe(L-1)(CO)(H)(carboxylic acid) of 0.015 M was obtained after 15 min of stirring.

In a glow box under argon, test tubes were charged with KBF$_4$ (10 mol %) or without. Then acetophenone (1 ml at 3M, 3.0 mmol) was added following by Fe(L-1)(CO)(H)(OC(O)R) (1 mL at 0.015M, 0.015 mmol). The tubes were then placed in a parallel hydrogenation apparatus and heated to the corresponding temperature, then pressurised with hydrogen gas at 20 bar and mechanically stirred. After 8 h, the parallel hydrogenation apparatus was cooled to room temperature, depressurized, and each tube analysed by GC (DB-Wax).

Under these conditions several complexes Fe(L-1)(CO)(H)(OC(O)R) as reported in Table 3 were tested. The results are reported in Table 4.

TABLE 3

Structure and names of carboxylic acids used with carbonyl amido bis[2-(di-isopropylphosphino)ethyl] amine iron (II) complex (Fe(L-1-H)(CO)(H)) to generate in situ the complex Fe(L-1)(CO)(H)(OC(O)R).

| Carboxylic Acid | Structure | Name |
|---|---|---|
| CA1 | [structure] | Formic acid |
| CA2 | [structure] | Acetic acid |

TABLE 3-continued

Structure and names of carboxylic acids used with carbonyl amido bis[2-(di-isopropylphosphino)ethyl] amine iron (II) complex (Fe(L-1-H)(CO)(H)) to generate in situ the complex Fe(L-1)(CO)(H)(OC(O)R).

| Carboxylic Acid | Structure | Name |
|---|---|---|
| CA3 | 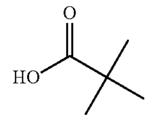 | Pivalic acid |
| CA4 | 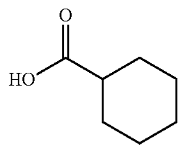 | Cyclohexanecarboxylic acid |
| CA5 | 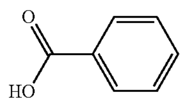 | Benzoic acid |
| CA6 | 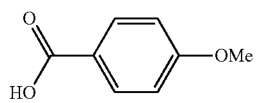 | 4-Methoxybenzoic acid |
| CA7 | 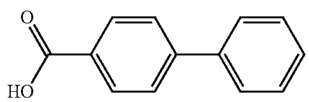 [SMILES: O=C(O)c1ccc(-c2ccccc2)cc1] | 4-phenylbenzoic acid |
| CA8 | 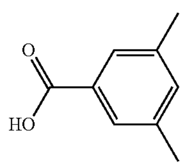 | 3,5-dimethylbenzoic acid |

TABLE 4

Hydrogenation of acetophenone using complexes Fe(L-1)(CO)(H)(OC(O)R) formed in situ from the corresponding carboxylic acid and the carbonyl amido bis[2-(di-isopropylphosphino)ethyl] amine iron (II), (Fe(L-1-H)(CO)(H)) complex.

| Test | Carboxylic Acid | C/MX2 | T (° C.) | Conv. | ROH |
|---|---|---|---|---|---|
| 1 | CA1 | 5000/0 | 50 | 73 | 73 |
| 2 | CA1 | 5000/100000 | 50 | >99 | >99 |
| 3 | CA2 | 5000/0 | 100 | 91 | 91 |
| 4 | CA2 | 5000/100000 | 100 | >99 | 99 |
| 5 | CA3 | 5000/0 | 80 | 39 | 39 |
| 6 | CA3 | 5000/100000 | 100 | 85 | 85 |
| 7 | CA4 | 5000/0 | 100 | 56 | 56 |
| 8 | CA4 | 5000/100000 | 100 | 76 | 7676 |
| 9 | CA5 | 5000/0 | 100 | 10 | 10 |
| 10 | CA5 | 5000/100000 | 100 | 36 | 36 |
| 11 | CA6 | 5000/0 | 100 | 39 | 39 |
| 12 | CA6 | 5000/100000 | 100 | 94 | 94 |
| 13 | CA7 | 5000/0 | 100 | 7 | 7 |
| 14 | CA7 | 5000/100000 | 100 | 88 | 88 |
| 15 | CA8 | 5000/0 | 100 | 21 | 21 |
| 16 | CA8 | 5000/100000 | 100 | >99 | >99 |

C/MX2: Catalyst/KBF$_4$ ratio in ppm relative to the substrate.
Conv.: Conversion (in %, analysed by GC) of acetophenone to the corresponding 1-phenyl ethanol after 8 h. Reaction conditions: H$_2$ gas (20 bar), 50° C.-100° C., THF (1.5M).
ROH: amount of 1-phenyl ethanol in percent in the reaction mixture as analysed by GC Example 9

Catalytic Hydrogenation of Acetophenone Using Complexes Fe(L-1)(CO)(H)(OC(O)R) with Various Salts of Formula MX Following, the typical procedure as described in Example 8. Under these conditions several salts of formula MX as reported in Table 5 were tested. The results are reported in Table 6.

TABLE 5

Structure and names of salts of formula MX used with carbonyl hydridoformate bis[2-(di-isopropylphosphino)ethyl] amine iron (II), (Fe(L-1)(CO)(H)(OC(O)H)) or with carbonyl hydridoacetate bis[2-(di-isopropylphosphino)ethyl] amine iron (II), (Fe(L-1)(CO)(H)(OC(O)Me)) (generated in situ).

| MX | Structure | Name |
|---|---|---|
| MX1 | NaBF$_4$ | Sodium tetrafluoroborate |
| MX2 | KBF$_4$ | Potassium tetrafluoroborate |
| MX3 | CsBF$_4$ | Cesium tetrafluoroborate |
| MX4 | KOTf | Potassium triflate |
| MX5 | KPF$_6$ | Potassium hexafluorophosphate |
| MX6 | K$_3$PO$_4$ | Potassium phosphate |
| MX7 | LiF | Lithium fluoride |

TABLE 6

Hydrogenation of acetophenone using complexes Fe(L-1)(CO)(H)(OC(O)R) formed in situ from the corresponding carboxylic acid and the carbonyl amido bis[2-(di-isopropylphosphino)ethyl] amine iron (II), (Fe(L-1-H)(CO)H) complex with the corresponding MX.

| Test | MX | Complexes | C/MX | T (° C.) | Conv. | ROH |
|---|---|---|---|---|---|---|
| 1 | — | C1 | 5000/0 | 50 | 73 | 73 |
| 2 | MX1 | C1 | 5000/100000 | 50 | >99 | >99 |
| 3 | MX2 | C1 | 5000/100000 | 50 | >99 | >99 |
| 4 | MX2 | C1 | 2500/50000 | 50 | 76 | 76 |
| 5 | MX3 | C1 | 5000/100000 | 50 | >99 | >99 |
| 6 | MX4 | C1 | 2500/50000 | 50 | 24 | 24 |
| 7 | MX5 | C1 | 2500/50000 | 50 | 13 | 13 |
| 8 | MX6 | C1 | 5000/100000 | 50 | >99 | >99 |
| 9 | MX7 | C1 | 5000/100000 | 50 | 92 | 91 |
| 10 | MX2 | C2 | 5000/100000 | 100 | 85 | 85 |
| 11 | — | C3 | 5000/100000 | 80 | 24 | 24 |
| 12 | — | C3 | 5000/100000 | 100 | 91 | 91 |
| 13 | MX2 | C3 | 5000/100000 | 100 | 99 | 99 |

C/MX: Catalyst/MX ratio in ppm relative to the substrate.
Conv.: Conversion (in %, analysed by GC) of acetophenone to the corresponding 1-phenyl ethanol after 8 h. Reaction conditions: H$_2$ gas (20 bar), 50° C.-100° C., THF (1.5M).
ROH: amount of 1-phenyl ethanol in percent in the reaction mixture as analysed by GC Example 10

Catalytic Hydrogenation of Acetophenone Using Complexes Fe(L-1)(CO)(H)(OC(O)R) with Different Solvents A typical experimental procedure is as follows:
In a glow box under argon, test tubes were charged successively with Fe(L-1)(CO)(H)(OC(O)R) (0.5 mol %) and then with a solution of acetophenone (3 mmol) in the corresponding solvent (2 mL). The tubes were then placed in a parallel hydrogenation apparatus and heated to the corresponding temperature, then pressurised with hydrogen gas at 20 bar and mechanically stirred. After 8 h, the parallel hydrogenation apparatus was cooled to room temperature, depressurized, and each tube analysed by GC (DB-Wax).

Under these conditions several solvent with complexes Fe(L-1)(CO)(H)(OC(O)R) were tested. The results are reported in Table 7.

TABLE 7

Hydrogenation of acetophenone using isolated complexes Fe(L-1)(CO)(H)(OC(O)R) with different solvents

| Test | Complexes | C | T (° C.) | Solvent | Conv. | ROH |
|---|---|---|---|---|---|---|
| 1 | C1 | 5000 | 50 | Ethanol | 42 | 42 |
| 2 | C1 | 5000 | 50 | Isopropanol | 97 | 97 |
| 3 | C1 | 5000 | 50 | Tetrahydrofuran | >99 | >99 |
| 4 | C1 | 5000 | 50 | Heptane | >99 | >99 |
| 5 | C1 | 5000 | 50 | Toluene | >99 | >99 |
| 6 | C1 | 2500 | 50 | Toluene | 57 | 57 |
| 7 | C2 | 5000 | 100 | Ethanol | 35 | 35 |
| 8 | C2 | 5000 | 100 | Isopropanol | 56 | 56 |
| 9 | C2 | 5000 | 100 | Tetrahydrofuran | 89 | 89 |
| 10 | C2 | 5000 | 100 | Heptane | 47 | 47 |
| 11 | C2 | 5000 | 100 | Toluene | 48 | 48 |

C: Catalyst ratio in ppm relative to the substrate.
Conv.: Conversion (in %, analysed by GC) of acetophenone to the corresponding 1-phenyl ethanol after 8 h. Reaction conditions: $H_2$ gas (20 bar), 50° C. or 100° C., Solvent (1.5M).
ROH: amount of 1-phenyl-ethanol in percent in the reaction mixture as analysed by GC Example 11

Catalytic Hydrogenation of Aldehydes and Ketones with Complex Fe(L-1)(CO)(H)(OC(O)H) (C1)

A typical experimental procedure is as follows:

In the glow box under argon, test tubes were charged successively with Fe(L-1)(CO)(H)(OC(O)H) (0.5 mol %) and with $KBF_4$ (10 mol %) or without. Then the corresponding ketones or aldehydes (3 mmol) dissolved in THF (2 mL) was added. The tubes were then placed in a parallel hydrogenation apparatus and heated to the corresponding temperature, then pressurised with hydrogen gas at 20 bar and mechanically stirred. After 16 h, the parallel hydrogenation apparatus was cooled to room temperature, depressurized, and each tube analysed by GC (DB-Wax) showing the conversions into the corresponding alcohols.

Under these conditions several aldehydes and ketones as reported in Table 8 were tested. The results are reported in Table 9.

TABLE 8

Structure and names of aldehydes and ketones.

| Substrate | Structure | Name |
|---|---|---|
| 1 | | Acetophenone |
| 2 | | Cyclohexanone |
| 3 | 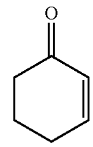 | Cyclohexenone |
| 4 | 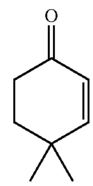 | 4,4-Dimethylcyclohex-2-enone |
| 5 | 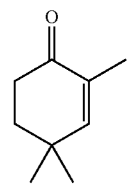 | 2,4,4-Trimethylcyclohexenone |
| 6 | 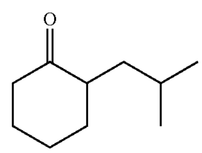 | 6,6-Dimethylcyclohex-2-enone |
| 7 | 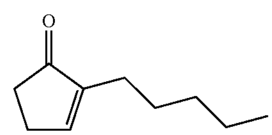 | 2-Pentylcyclopent-2-enone |
| 8 | 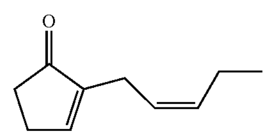 | (Z)-2-(Pent-2-enyl)cyclopent-2-enone |
| 9 | 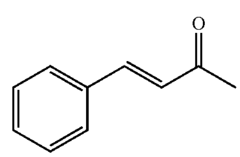 | (E)-4-Phenylbut-3-en-2-one |
| 10 | 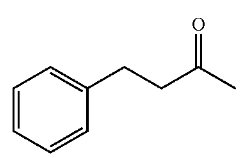 | 4-Phenylbutan-2-one |
| 11 | 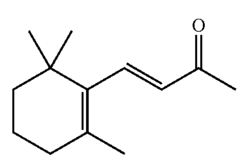 | (E)-4-(2,6,6-Trimethylcyclohexenyl)but-3-en-2-one |
| 12 | 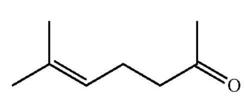 | 6-Methylhept-5-en-2-ol |

TABLE 8-continued

Structure and names of aldehydes and ketones.

| Substrate | Structure | Name |
|---|---|---|
| 13 | 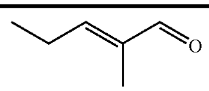 | 2-Methylpent-2-enal |
| 14 | 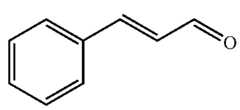 | Cinnamaldehyde |

TABLE 9

Hydrogenation of different aldehydes and ketones using complex carbonyl hydridoformate bis[2-(di-isopropylphosphino)ethyl] amine iron (II), (Fe(L-1)(CO)(H)(OC(O)H)).

| Test | Sub. | T (° C.) | C1/MX2 | Conv. | ROH | Sel. |
|---|---|---|---|---|---|---|
| 1 | 1 | 50 | 5000/0 | >99 | >99 | — |
| 2 | 1 | 50 | 2500/100000 | >99 | >99 | — |
| 3 | 2 | 50 | 5000/100000 | >99 | >99 | — |
| 4 | 3 | 50 | 5000/100000 | >99 | 95 | 95:5 |
| 5 | 4 | 100 | 5000/100000 | >99 | 96 | 99:1 |
| 6 | 5 | 100 | 5000/100000 | 98 | 97 | >99 |
| 7 | 6 | 100 | 5000/100000 | >99 | 99 | — |
| 8 | 7 | 80 | 5000/100000 | >99 | 71 | 72:28 |
| 9 | 8 | 80 | 5000/100000 | 87.3 | 72 | 86:14 |
| 10 | 9 | 50 | 5000/100000 | 98 | 89 | 96:4 |
| 11 | 10 | 100 | 5000/100000 | >99 | 99 | — |
| 12 | 11 | 50 | 5000/100000 | 44 | 42 | >99 |
| 13 | 12 | 50 | 5000/100000 | 46 | 46 | >99 |
| 14 | 13 | 50 | 5000/100000 | >99 | 98 | >99 |
| 15 | 14 | 50 | 5000/100000 | >99 | >99 | >99 |

C1/MX2: Catalyst/KBF$_4$ ratio in ppm relative to the substrate.
Conv.: Conversion (in %, analysed by GC) of the corresponding aldehydes or ketones into the corresponding alcohol after 16 hour. Reaction conditions: H$_2$ gas (20 bar), 50-100° C., THF (1.5M).
ROH: amount of alcohol in percent in the reaction mixture as analysed by GC
Sel.: Selectivity given as ratio between unsaturated and saturated alcohol as analysed by GC.

Example 12

Catalytic Hydrogenation of Aldehydes and Ketones with Complex Fe(L-1)(CO)(H)(OC(O)Me) (C3)

Following, the typical procedure as described in Example 11, where complex Fe(L-1)(CO)(H)(OC(O)H) was replaced by complex Fe(L-1)(CO)(H)(OC(O)Me).

Under these conditions several aldehydes and ketones as reported in Table 8 were tested. The results are reported in Table 10.

TABLE 10

Hydrogenation of different aldehydes and ketones using complex carbonyl hydridoacetate bis[2-(di-isopropylphosphino)ethyl] amine iron (II), (Fe(L-1)(CO)(H)(OC(O)Me)).

| Test | Sub. | T (° C.) | C3/MX2 | Conv. | ROH | Sel. |
|---|---|---|---|---|---|---|
| 1 | 1 | 100 | 5000/100000 | >99 | 99 | — |
| 2 | 2 | 100 | 5000/100000 | >99 | >99 | — |
| 3 | 3 | 100 | 5000/100000 | 97 | 82 | 99:1 |
| 4 | 4 | 100 | 5000/100000 | 82 | 81 | 99.6:0.4 |
| 5 | 9 | 100 | 5000/100000 | >99 | 86 | 88:12 |
| 6 | 11 | 100 | 5000/100000 | 31 | 20 | >99 |
| 7 | 12 | 100 | 5000/100000 | 34 | 33 | >99 |
| 8 | 13 | 100 | 5000/100000 | >99 | 91 | >99 |
| 9 | 14 | 100 | 5000/100000 | >99 | 99 | >99 |

C3/MX2: Catalyst/KBF$_4$ ratio in ppm relative to the substrate.
Conv.: Conversion (in %, analysed by GC) of the corresponding aldehydes or ketones into the corresponding alcohol after 16 hour. Reaction conditions: H$_2$ gas (20 bar), 50-100° C., THF (1.5M).
ROH: amount of alcohol in percent in the reaction mixture as analysed by GC.
Sel.: Selectivity given as ratio between unsaturated and saturated alcohol as analysed by GC.

Example 13

Catalytic Hydrogenation of Aldehydes and Ketones with Complex Fe(L-1)(CO)(H)(OC(O)$^t$Bu) (C2)

Following, the typical procedure as described in Example 11, where complex Fe(L-1)(CO)(H)(OC(O)H) was replaced by (Fe(L-1)(CO)(H)OC(O)$^t$Bu)).

Under these conditions several aldehydes and ketones as reported in Table 8 were tested. The results are reported in Table 11.

TABLE 11

Hydrogenation of different aldehydes and ketones using complex carbonyl hydridopivalate bis[2-(di-isopropylphosphino)ethyl] amine iron (II) (Fe(L-1)(CO)(H)(OC(O)$^t$Bu)).

| Test | Sub. | T (° C.) | C2/MX2 | Conv. | ROH | Sel. |
|---|---|---|---|---|---|---|
| 1 | 1 | 100 | 5000/100000 | 89 | 89 | — |
| 2 | 2 | 100 | 5000/100000 | >99 | >99 | — |
| 3 | 3 | 100 | 5000/100000 | >99 | 78 | 81:19 |
| 4 | 4 | 100 | 5000/100000 | 41 | 36 | >99 |
| 5 | 6 | 100 | 5000/100000 | 40 | 35 | — |
| 6 | 9 | 100 | 5000/100000 | >99 | 86 | 89:11 |
| 7 | 10 | 100 | 5000/100000 | 29 | 28 | — |
| 8 | 11 | 100 | 5000/100000 | 48 | 45 | >99 |
| 9 | 12 | 100 | 5000/100000 | 37 | 35 | >99 |
| 10 | 13 | 100 | 5000/100000 | >99 | 93 | >99 |
| 11 | 14 | 100 | 5000/100000 | >99 | 98 | >99 |

C2/MX2: Catalyst/KBF$_4$ ratio in ppm relative to the substrate.
Conv.: Conversion (in %, analysed by GC) of the corresponding aldehydes or ketones into the corresponding alcohol after 16 hour. Reaction conditions: H$_2$ gas (20 bar), 100° C., THF (1.5M).
ROH: amount of alcohol in percent in the reaction mixture as analysed by GC
Sel.: Selectivity given as ratio between unsaturated and saturated alcohol as analysed by GC.

Example 14

Comparative Catalytic Hydrogenation of Aldehydes and Ketones with Prior Art Complex (Fe(L-1)(CO)(H)(BH$_4$) (C5)

Following, the typical procedure as described in Example 11, where complex Fe(L-1)(CO)(H)(OC(O)H) was replaced by complex Fe(L-1)(CO)(H)(BH$_4$).

Under these conditions several aldehydes and ketones as reported in Table 8 were tested. The results are reported in Table 12.

TABLE 12

Hydrogenation of different aldehydes and ketones using complex carbonyl hydrido borohydride bis[2-(di-isopropylphosphino)ethyl] amine iron (II) (Fe(L-1)(CO)(H)(BH$_4$) (C5)) compared to complex of the present invention (Fe(L-1)(CO)(H)(OC(O)H) (C1), (Fe(L-1)(CO)(H)(OC(O)Me) (C3) or (Fe(L-1)(CO)(H)(OC(O)$^t$Bu) (C2)).

| Test | Sub. | Complex | T (° C.) | C/MX2 | Conv. | ROH | Sel. |
|---|---|---|---|---|---|---|---|
| 1 | 3 | C1 | 50 | 5000/100000 | >99 | 95 | 95:5 |
| 2 | 3 | C2 | 100 | 5000/100000 | 97 | 82 | 99:1 |
| 3 | 3 | C5 | 50 | 1000/0 | >99 | 89 | 89:11 |
| 4 | 8 | C1 | 80 | 5000/100000 | 87 | 72 | 86:14 |
| 5 | 8 | C5 | 50 | 5000/0 | 99 | 55 | 57:43 |
| 6 | 9 | C1 | 50 | 5000/100000 | 98 | 89 | 96:4 |
| 7 | 9 | C2 | 100 | 5000/100000 | >99 | 86 | 89:11 |
| 8 | 9 | C3 | 100 | 5000/100000 | >99 | 86 | 88:12 |
| 9 | 9 | C5 | 50 | 5000/0 | >99 | 40 | 40:60 |
| 10 | 14 | C1 | 50 | 5000/100000 | >99 | 99 | >99 |
| 11 | 14 | C2 | 100 | 5000/100000 | >99 | 98 | >99 |
| 12 | 14 | C3 | 100 | 5000/100000 | >99 | 99 | >99 |
| 13 | 14 | C5 | 50 | 5000/0 | >99 | 98 | 98.1:1.9 |

C/MX2: Catalyst/KBF$_4$ ratio in ppm relative to the substrate.
Conv.: Conversion (in %, analysed by GC) of the corresponding aldehydes or ketones into the corresponding alcohol after 16 hour. Reaction conditions: H$_2$ gas (20 bar), 50-100° C., THF (1.5M).
ROH: amount of alcohol in percent in the reaction mixture as analysed by GC
Sel.: Selectivity given as ratio between unsaturated and saturated alcohol as analysed by GC.

Example 15

Comparative Catalytic Hydrogenation of Aldehydes and Ketones with Complexes C1 (Fe(L-1)(CO)(H)(OC(O)H)) and Fe(L-1)(CO)(H)(C1) with MX or Basic Activation Modes Following, the typical procedure as described in Example 11.

Under these conditions several aldehydes and ketones as reported in Table 8 were tested. The results are reported in Table 13.

TABLE 13

Hydrogenation of different aldehydes and ketones using complexes C1 (Fe(L-1)(CO)(H)(OC(O)H)), and Fe(L-1)(CO)(H)(C1) with MX2 or basic activation modes.

| Test | Sub. | Complexes | T (° C.) | C | B | MX2 | Conv. | ROH | Sel. |
|---|---|---|---|---|---|---|---|---|---|
| 1 | 1 | C1 | 50 | 5000 | — | 100000 | >99 | 95 | 95:5 |
| 2 | 1 | Fe(L-1)(CO)(H)Cl | 50 | 5000 | 100000 | — | >99 | — | Poly. |
| 3 | 1 | Fe(L-1)(CO)(H)Cl | 50 | 5000 | — | 100000 | 0.4 | 0.4 | >99 |
| 4 | 4 | C1 | 100 | 5000 | — | 100000 | >99 | 96 | >99 |
| 5 | 4 | Fe(L-1)(CO)(H)Cl | 100 | 5000 | 100000 | — | 99 | 14 | 25:85 |
| 6 | 8 | C1 | 80 | 5000 | — | 100000 | >99 | 71 | 72:28 |
| 7 | 8 | Fe(L-1)(CO)(H)Cl | 80 | 5000 | 100000 | — | >99 | — | Poly. |
| 8 | 15 | C1 | 50 | 5000 | — | 100000 | >99 | 98 | 0:99 |
| 9 | 15 | Fe(L-1)(CO)(H)Cl | 50 | 5000 | 100000 | — | >99 | 4 | Poly. |

C: Catalyst in ppm relative to the substrate.
MX2: KBF$_4$ in ppm relative to the substrate
B: Base (tBuOK) in ppm relative to the substrate
Conv.: Conversion (in %, analysed by GC) of the corresponding aldehydes or ketones into the corresponding alcohol after 16 hour. Reaction conditions: H$_2$ gas (20 bar), 50-80° C., THF (1.5M).
ROH: amount of alcohol in percent in the reaction mixture as analysed by GC.
Sel.: Selectivity given as ratio between unsaturated and saturated alcohol as analysed by GC.
Poly.: Polymerisation Example 16

Catalytic Hydrogenation of Acetophenone Using Complexes Fe(L-1)(CO)(H)(OR) Generated In-Situ A typical experimental procedure is as follows:
Solutions Stock:
A solution of complex Fe(L-1)(CO)H 0.015M in THF.
A solution of 3M of acetophenone in THF.

In a glow box under argon, test tubes were charged with KBF$_4$ (10 mol %) or without. Then a solution of Fe(L-1-H)(CO)(H) (1 mL at 0.015M, 0.015 mmol) was added followed by the corresponding alcohol (0.25 ml) and THF (0.75 ml). Finally, acetophenone (1 ml at 3M, 3.0 mmol) was added and the tubes were then placed in a parallel hydrogenation apparatus and heated to the corresponding temperature, then pressurised with hydrogen gas at 20 bar and mechanically stirred. After 1 h, the parallel hydrogenation apparatus was cooled to room temperature, depressurized, and each tube analysed by GC (DB-Wax).

Under these conditions several complexes Fe(L-1)(CO)(H)(OR) as reported in Table 14 were tested. The results are reported in Table 15.

TABLE 14

Structure and names of alcohols used with carbonyl amido bis[2-(di-isopropylphosphino)ethyl] amine iron (II) complex (Fe(L-1-H)(CO)(H)) to generate in situ the complex Fe(L-1)(CO)(H)(OR).

| Alcohol | Structure | Name |
|---|---|---|
| A1 | (structure: 2-methylbutan-2-ol) | 2-Methylbutan-2-ol |
| A2 | (structure: 2-propanol) | 2-Propanol |

TABLE 14-continued

Structure and names of alcohols used with carbonyl amido bis[2-(di-isopropylphosphino)ethyl] amine iron (II) complex (Fe(L-1-H)(CO)(H)) to generate in situ the complex Fe(L-1)(CO)(H)(OR).

| Alcohol | Structure | Name |
|---------|-----------|------|
| A3 | ⌒OH | Ethanol |
| A4 | MeOH | Methanol |

TABLE 15

Hydrogenation of acetophenone using complexes Fe(L-1)(CO)(H)(OR) formed in situ from the corresponding alcohol and the carbonyl amido bis[2-(di-isopropylphosphino)ethyl] amine iron (II), (Fe(L-1-H)(CO)(H)) complex.

| Test | Alcohol | C/A/MX2 | T (° C.) | Time | Conv. | ROH |
|------|---------|---------|----------|------|-------|-----|
| 1 | A1 | 500/800000/0 | 100 | 1 | 6 | 6 |
| 2 | A1 | 500/800000/100000 | 100 | 1 | 8 | 8 |
| 3 | A2 | 500/1100000/0 | 100 | 1 | 11 | 11 |
| 4 | A2 | 500/1100000/100000 | 100 | 1 | 14 | 14 |
| 5 | A3 | 500/1400000/0 | 100 | 1 | 14 | 14 |
| 6 | A3 | 500/1400000/100000 | 100 | 1 | 40 | 40 |
| 7 | A4 | 500/2100000/0 | 100 | 1 | 15 | 15 |
| 8 | A4 | 500/2100000/100000 | 100 | 1 | 97 | 97 |
| 9 | A4 | 500/2100000/100000 | 100 | 8 | >99 | >99 |
| 10 | A4 | 50/2100000/100000 | 100 | 24 | 3 | 3 |
| 11 | A4 | 100/2100000/100000 | 100 | 24 | 45 | 45 |
| 12 | A4 | 200/2100000/100000 | 100 | 24 | >99 | >99 |
| 13 | A4 | 500/2100000/100000 | 50 | 24 | 88 | 88 |
| 14 | A4 | 500/2100000/100000 | 80 | 24 | 99 | 99 |
| 15[a] | A4 | 500/2100000/100000 | 50 | 24 | 42 | 42 |
| 16[a] | A4 | 500/2100000/100000 | 100 | 24 | >99 | >99 |

C/A/MX2: Catalyst/Alcohol/KBF$_4$ ratio in ppm relative to the substrate.
Conv.: Conversion (in %, analysed by GC) of acetophenone to the corresponding 1-phenyl ethanol after the indicated time (h). Reaction conditions: H$_2$ gas (20 bar), 50° C.-100° C., THF (1M).
ROH: amount of 2-phenyl ethanol formed in percent in the reaction mixture as analysed by GC
[a]Reactions performed under H$_2$ gas (5 bar).

What is claimed is:

1. A process for the reduction by hydrogenation, using molecular H$_2$, of a C$_3$-C$_{70}$ substrate containing one or two ketone or aldehyde groups into the corresponding alcohol, or diol,
wherein the process is carried out in the presence of at least one catalyst in the form of an iron complex of formula $$[Fe(L3)(L')(Y)(Z)] \quad (1)$$

wherein L3 represents a tridentate ligand wherein the coordinating groups consist of one amino or imino group and two phosphino groups;
L' represents a CO or C$_{1-11}$ isonitrile compound;
Y represents a hydrogen atom or a C$_1$-C$_{14}$ carboxylic radical;
Z represents a hydroxyl group, a C$_1$-C$_{14}$ carboxylic radical or a linear C$_1$-C$_{14}$ alkoxy radical; and
optionally a salt of formula MX wherein M is an alkali metal cation and X is a non-coordinating mono anion, wherein the process is performed in the absence of a base.

2. The process according to claim 1, wherein the ligand L3 is a compound of formula

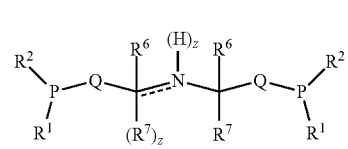

(A)

wherein the dotted line indicates a single or double bond;
z is 0 or 1 when the carbon-nitrogen bond with the dotted line represents a double or single bond respectively;
R$^1$ and R$^2$, when taken separately, represent, simultaneously or independently, a linear, branched or cyclic C$_1$ to C$_{10}$ alkyl or alkenyl group optionally substituted, a C$_6$ to C$_{10}$ aromatic group optionally substituted; the groups R$^1$ and R$^2$, when taken together, may form a saturated or unsaturated ring optionally substituted, having 5 to 10 atoms and including the phosphorus atom to which the R$^1$ and R$^2$ groups are bonded;
R$^6$ and R$^7$ represent, simultaneously or independently, a hydrogen atom, a linear, branched or cyclic C$_1$ to C$_6$ alkyl or alkenyl group optionally substituted, a C$_6$-C$_{10}$ aromatic group optionally substituted; when the dotted line represent a single bond, two R$^6$ taken together, may form a saturated heterocycle, optionally substituted and optionally containing one or two additional nitrogen or oxygen atoms, containing 5 to 10 atoms and including the N atom and the carbon atoms to which the R$^6$ groups are bonded respectively; and
Q represents:
a group of formula

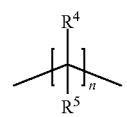

(i)

wherein n is an integer from 1 to 3, and
R$^4$ and R$^5$ represent, simultaneously or independently, a hydrogen atom, a linear, branched or cyclic C$_1$ to C$_6$ alkyl or alkenyl group optionally substituted, a C$_6$-C$_{10}$ aromatic group optionally substituted; two distinct R$^4$ and/or R$^5$ groups, taken together, may form a Cs to Cs, saturated ring optionally substituted, including the carbon atoms to which each of the R$^4$ or R$^5$ group is bonded; or
a diphenyl, dinaphthyl, C$_5$-C$_{12}$ metallocediyl, phenylene or naphthylene group optionally substituted; and
the optional substituents of R$^4$, R$^5$, R$^6$ and R$^7$ are one or two halogen, C$_1$ to C$_{10}$ alkoxy groups, halo- or perhalo-hydrocarbon, COOR, NR$_2$, quaternary amine or R groups, wherein R is a C$_1$ to C$_6$ alkyl, or a C$_5$ to C$_{12}$ cycloalkyl, aralkyl or aromatic group, the latter being also optionally substituted by one, two or three halogen, sulfonates groups or C$_1$-C$_8$ alkyl, alkoxy, amino, nitro, sulfonates, halo- or perhalo-hydrocarbon or ester groups; and
the optional substituents of R$^1$ and R$^3$ and Q, in particular when the groups are or contains phenyl or aromatic groups or moieties, one to three C$_1$ to C$_5$ alkoxy groups, C$_1$ to C$_4$ alkyl groups, or NR groups, wherein R is a C$_1$ to C$_6$ alkyl C$_5$ to C$_6$ cycloalkyl.

3. The process according to claim 1, wherein the ligand L3 is a compound of formula

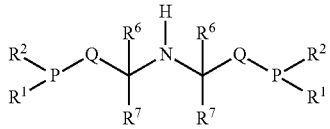

(B)

wherein Q represents:
a group of formula

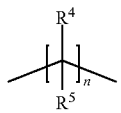

(i)

wherein n is an integer from 1 to 3, and

R$^4$ and R$^5$ represent, simultaneously or independently, a hydrogen atom, a linear, branched or cyclic C$_1$ to C$_6$ alkyl or alkenyl group optionally substituted, a C$_6$-C$_{10}$ aromatic group optionally substituted; two distinct R$^4$ and/or R$^5$ groups, taken together, may form a Cs to Cs, saturated ring optionally substituted, including the carbon atoms to which each of the R$^4$ or R$^5$ group is bonded; or a diphenyl, dinaphthyl, C$_5$-C$_{12}$ metallocediyl, phenylene or naphthylene group optionally substituted; and the optional substituents of R$^4$, R$^5$, R$^6$ and R$^7$ are one or two halogen, C$_1$ to C$_{10}$ alkoxy groups, halo- or perhalo-hydrocarbon, COOR, NR$_2$, quaternary amine or R groups, wherein R is a C$_1$ to C$_6$ alkyl, or a C$_5$ to C$_{12}$ cycloalkyl, aralkyl or aromatic group, the latter being also optionally substituted by one, two or three halogen, sulfonates groups or C$_1$-C$_8$ alkyl, alkoxy, amino, nitro, sulfonates, halo- or perhalo-hydrocarbon or ester groups; and the optional substituents of R$^1$ and R$^3$ and Q, in particular when the groups are or contains phenyl or aromatic groups or moieties, one to three C$_1$ to C$_5$ alkoxy groups, C$_1$ to C$_4$ alkyl groups, or NR groups, wherein R is a C$_1$ to C$_6$ alkyl Cs to C$_6$ cycloalkyl.

4. The process according to claim 1, wherein the substrate is a C$_5$-C$_{30}$ compound of formula

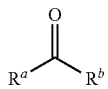

(I)

wherein R$^a$ and R$^b$, taken together, represent a C$_3$-C$_{20}$, preferably C$_4$-C$_{20}$, hydrocarbon group, optionally substituted and optionally comprising one, two or three oxygen or nitrogen atoms; or, when the R$^a$ and R$^b$ are taken separately, R$^a$ represents a hydrogen atom or a R$^b$ group; and R$^b$ represents a C$_1$-C$_{30}$ hydrocarbon group, optionally substituted and optionally comprising one, two or three oxygen or nitrogen atoms.

5. The process according to claim 4, wherein the substrate is a compound of formula (I) wherein R$^a$ represent a hydrogen atom or a R$^b$ group, and each R$^b$, when taken separately, represent simultaneously or independently a linear, branched or cyclic C$_3$-C$_{18}$ aromatic, alkyl, alkenyl or alkanedienyl group optionally substituted; or R$^a$ and R$^b$ are bonded together and form a C$_5$-C$_{20}$ saturated or unsaturated linear, branched, mono-, di- or tri-cyclic group, optionally substituted.

6. The process according to claim 1, wherein the MX is selected from the group consisted of NaBF$_4$, KBF$_4$, or CsBF$_4$.

7. The process according to claim 1, wherein Y represents a hydrogen atom.

8. The process according to claim 1, wherein Z represents a formate, an acetate or a pivalate radical.

9. The process according to claim 1, wherein Z represents a methoxy radical.

* * * * *